United States Patent [19]

Bombardelli

[11] Patent Number: 5,334,385
[45] Date of Patent: Aug. 2, 1994

[54] NEW ALKALOID DERIVATIVES, THEIR USE AND PHARMACEUTICAL FORMULATIONS CONTAINING THEM

[75] Inventor: Ezio Bombardelli, Milan, Italy

[73] Assignee: Indena S.p.A., Italy

[21] Appl. No.: 922,689

[22] Filed: Jul. 30, 1992

[30] Foreign Application Priority Data

Jun. 2, 1992 [GB] United Kingdom ............ 9211659.9

[51] Int. Cl.$^5$ .................. A61K 35/78; A61K 7/00
[52] U.S. Cl. .................. 424/195.1; 424/401; 554/79
[58] Field of Search .............. 424/450, 401, 195.1; 554/79, 282

[56] References Cited

U.S. PATENT DOCUMENTS

| 2,935,448 | 5/1960 | Calter | 554/79 |
| 4,254,115 | 5/1981 | Dawidson | 554/79 |
| 4,818,533 | 4/1989 | Boulware | 424/195.1 |
| 4,830,028 | 5/1989 | Lawson | 546/282 |
| 4,842,865 | 5/1989 | Durr | 424/450 |
| 4,844,901 | 7/1989 | Keplinger | 424/195.1 |
| 4,952,408 | 8/1990 | Kahman | 424/450 |
| 5,009,819 | 4/1991 | Popescu | 264/4.1 |

Primary Examiner—Thurman K. Page
Assistant Examiner—Sally Gardner
Attorney, Agent, or Firm—Kirschstein, Ottinger, Israel & Schiffmiller

[57] ABSTRACT

Salts of a pharmacologically active, naturally occurring or synthetic alkaloids, or alkaloid derivatives and a phosphatidic acid are provided, which preferably have the formula $$[Alk]_x[PA]_y$$

wherein
Alk represents a cation derived from said pharmacologically active, naturally occurring or synthetic alkaloid, or alkaloid derivative,
PA represents a phosphatidic acid or a mixture of different phosphatidic acids, and
x:y is from 2:1 to 1:2.

The therapeutic use of the salts of the invention in the treatment of syndromes affecting the elderly, particularly conditions that are related to changes in cerebral metabolism and reduced blood flow are decribed, as well as cosmetic methods.

11 Claims, No Drawings

NEW ALKALOID DERIVATIVES, THEIR USE AND PHARMACEUTICAL FORMULATIONS CONTAINING THEM

BACKGROUND OF THE INVENTION

The present invention relates to new alkaloid derivatives, to processes for their production and to novel pharmaceutical compositions and dosage forms containing them. More specifically, the present invention relates to the therapeutic use of new salts of indole alkaloids that are effective in the treatment of syndromes affecting the elderly, particularly conditions that are related to changes in cerebral metabolism and reduced blood flow.

Many naturally occurring alkaloids, synthetic alkaloid analogues and derivatives of naturally occurring alkaloids and alkaloid analogues have extensive use in pharmacology for treatment of numerous pathological conditions and also for inducing desired physiological states in healthy patients. Examples include the alkaloids used in the cardiovascular field, in obstetrics and in neurology.

In general alkaloids are nitrogenous bases that occur in plants, particularly those of the families *Papaveraceae, Apocynaceae, Papilonaceae, Ranunculaceae* and *Solanaceae*. Most alkaloids are characterised by the presence of one or more nitrogen atoms located in a heterocyclic ring system. General discussions of alkaloids are to be found in standard text books and particular reference is to be made, for example, to the Chapter entitled "Alkaloids" in Organic Chemistry, 3rd Edition, Fieser, L. F. and Fieser, M., Reinhold Publishing Corporation, 1956 and the Chapter entitled "Alkaloids and other Amino-Acid Derivatives" in The Biosynthesis of Natural Products, Bu'Lock, J. D., McGraw-Hill Publishing Company Limited, 1965 and in particular to "The Alkaloids Chemistry and Physiology, R. H. F. Marske and H. L. Holmes (Eds.), Academic Press Inc., Publishers.

Naturally occurring alkaloids generally have substituent groups which are susceptible to modification and derivatisation and synthetic alkaloids and derivatives of naturally occurring alkaloids may be prepared by, for example, subjecting a naturally occurring alkaloid to one or more of the following chemical modifications:
(i) esterification,
(ii) hydrolysis of an ester group,
(iii) salification,
(iv) conversion of a primary, secondary, or tertiary amino group respectively to a secondary, tertiary or quaternary amino group
(iv) epimerisation,
(vii) conversion of a salt to a free base,
(ix) etherification of a hydroxy group,
(x) conversion of an etherified hydroxy group to a free hydroxy group.

The term "synthetic alkaloid analogues and derivatives of naturally occurring alkaloids" as used herein is intended to include naturally occurring alkaloids which have been subjected to one or more of the above modification steps (i) to (x).

Typical alkaloids in widespread use include vincamine and apovincamine and their derivatives, raubasine, apocuanzine, nicergoline and hydergin.

A disadvantage of available alkaloids and alkaloid derivatives is that they generally are highly hydrophilic and consequently are not readily converted into dosage forms which are adapted to partition into the lipid phase. Also available dosage forms are not readily adapted for transcutaneous administration nor for formulation into convenient sustained release forms.

SUMMARY OF THE INVENTION

We have now developed a novel class of alkaloid derivatives which avoid these disadvantages.

Thus according to the present invention there are provided salts of phosphatidic acids and pharmacologically active, naturally occurring or synthetic alkaloids, or alkaloid derivatives.

The salts of the invention may be represented by the formula $$[Alk]_x[PA]_y \qquad \text{(III)}$$

wherein
Alk represents a cation derived from said pharmacologically active, naturally occurring or synthetic alkaloid, or alkaloid derivative,
PA represents a phosphatidic acid or a mixture of different phosphatidic acids, and
x:y is from 2:1 to 1:2.

Preferably the ratio x:y is from 1.2:1 to 1:1.2, most preferably from 1.1:1 to 1:1.1.

In the novel salts of the invention, the pharmacologically active, naturally occurring or synthetic alkaloid, or alkaloid derivative is an indole alkaloid, especially one of the classes referred to above.

The term "phosphatidic acid" as used herein, can represent a compound having the formula.

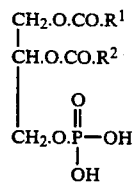

wherein $R_1$ and $R_2$, which may be the same or different, each represents a $C_{10-24}$ alkyl group, a $C_{10-24}$ alkenyl group, or a $C_{10-24}$ alkadienyl group. Said groups may be represented by the formulae $C_nH_{2+1}$, $C_nH_{2-1}$ or $C_nH_{2-3}$ Preferably, n is from 15 to 24, most preferably 15 or 17.

In more specific terms, the present invention relates to new salts of basic indole alkaloids with natural or synthetic phosphatidic acids that exhibit increased bioavailability when administered by mouth, rectally, transcutaneously or epicutaneously. For reasons explained below, the trancutaneous and transepidermal routes are the administration routes of choice for the new substances according to the invention.

An especially useful class of alkaloid salts according to the invention are ones prepared from alkaloids that act predominantly on the peripheral blood flow, such as vincamine, ethyl apovincaminate and its analogues, raubasine, nicergoline and ergot alkaloids that improve the cerebral metabolism or increase cerebral blood flow.

According to a further aspect of the invention there are provided pharmaceutical compositions comprising a salt according to the invention, preferably one of the preferred salts referred to above, and a pharmaceutically acceptable excipient.

The salts according to the invention are especially well adapted for formulation into sustained release pharmaceutical dosage forms capable of releasing their pharmacologically active substance (i.e. the pharmacologically active, naturally occurring or synthetic alkaloid, or alkaloid derivative) over a period of time and in particular to release the pharmaceutically active substance transcutaneously.

For this purpose, the sustained release forms are preferably in the form of a cutaneous patch, plaster or bandage.

The novel salts provided according to the invention are highly lipophilic and exhibit excellent bioavailability when administered orally, transcutaneously or transepidermally. The new salts are particularly valuable, when incorporated in plasters or appropriate gels or suitable pharmaceutical forms, in the treatment of peripheral circulatory disturbances of the brain and other parts of the body where increased blood flow improves organ function. The products are also suitable for use in the dermatological and cosmetic fields for the treatment of both surface and deep microcirculatory disturbances.

The salts of the invention may be prepared by a process conprising salification of (a) a pharmacologically active, naturally occurring or synthetic alkaloid, or alkaloid derivative and (b) one or more phosphatidic acids, each of said reactants (a) and (b) being in free form or in the form of a salt-forming derivative.

The salification is preferably carried out in a soluton for both reactants.

The solvent is preferably selected from halogenated hydrocarbons, ketones, ethers and mixtures thereof.

Suitable phosphatidic acids for use as salifying agents are natural or synthetic phosphatidic acids. In general these possess acyl chains (which may be the same or different and saturated or unsaturated) linked via an ester bond to the oxygen atoms of glycerol. Included are natural phosphatidic acids comprising compounds having different fatty acids present in the ratio corresponding to the natural ratio in the compounds from the plant or animal tissue from which they originate.

The salification is normally carried out in non-protic solvents, generally starting from alkaloids in the form of the free base or salified with weak acids and from free phosphatidic acid(s). Alternatively, the salification may be carried out using a trans-salification procedure (or double decomposition reaction) in which a salt of an alkaloid with an anion $X^-$ is reacted with a salt of a phosphatidic acid with a cation $Y^+$, wherein the salt $Y^+.X^-$ is essentially insoluble in the reaction medium. An example is the reaction of a hydrochloride of an alkaloid with a sodium or potassium salt of phosphatidic acid(s).

The salts of the pharmacologically active, naturally occurring or synthetic alkaloids, or alkaloid derivatives thus obtained are highly soluble in non-protic solvents, from which they can be isolated by concentration and if necessary evaporation to dryness or by insolubilisation in non-solvents such as hexane or petroleum ether.

The salts may normally be obtained by reacting the reagents in molar proportions (1M:1M). Salification is generally complete when complete solubility of the reagents in the chosen solvent is achieved.

When treated with water, the novel salts of the invention can adopt a micellar form and distribute themselves quantitatively in non-miscible lipophilic organic solvents. The salts of the invention are believed to acquire their lipophilic character from the ability of the acyl chains to wrap themselves around the most polar central nucleus i.e. the region of the molecule constituted by the pharmacologically active, naturally occurring or synthetic alkaloid, or alkaloid derivative, with the result that they can form a liposomal microdispersion in aqueous media.

It has surprisingly been found that when the novel salts of the invention are administered in the form of gelled aqueous microdispersions (lipogels), or incorporated in controlled release plasters applied to various parts of the body, they have considerable therapeutic advantages over the traditional dosage forms of alkaloids. It has been shown that in these dosage forms the new salts according to the invention have a different level of bioavailability, with an attendant positive effects on their activity.

It has also been found (and this constitutes one of the most important aspects of the invention) that when the lipophilic salts of the above alkaloids are applied in controlled-release formulations at the base of the neck adjacent to the bifurcation of the branches of the internal carotid and common carotid arteries, or below the ear adjacent to the deep carotid artery or the anterior auricular and posterior occipital arteries, they can maintain active levels of the drug in the brain for prolonged periods. This is a necessary requirement in the treatment of chronic diseases such as metabolic disturbances caused by changes in the microcirculation, which are common in the elderly. Application of the compounds of the invention in this way is particularly applicable to salts according to the invention wherein the alkaloid is nicergoline or adrenergic ethyl apovincaminate.

Salts of the alkaloids with phosphatidic acids in liposomal or pseudoliposomal form have been found, in accordance with the invention, to interact rapidly with the cell structures and diffuse rapidly through the tissues where they can easily gain access to the lumen of the arteries, through which they can travel to the site of action.

These new salts can be applied to the above sites in dosages of between 5 and 50 mg given as one or more doses per day depending on the individual receptor response.

It is clear that if consistent results are to be obtained in chronic degenerative diseases there must be a constant supply of the drug to the target organ in quantities sufficient to produce the required effect. This may be achieved using salts according to the invention.

Controlled-release transcutaneous pharmaceutical forms have proved suitable for the administration of the new salts according to the invention since they enable the drug to be directed to the target organ with minimal involvement of the peripheral organs.

Controlled-release plasters have proved to be particularly effective for this purpose since between 5 and 50 mg of salts of the various alkaloids can be incorporated in the reservoir. Liposomal forms of the same salt applied in the form of lipogels, with or without the presence of conventional phospholipids, have also proved effective. The plaster form has also proved extremely practical for long-term use, as is necessary in this case. However, the salts according to the invention can also be incorporated and administered in other conventional forms such as tablets, oily solutions, suppositories, etc.

The salts according to the invention can be applied in the form of aqueous microdispersions or lipogels of in conventional gels and emulsions to large areas of the body such as the upper and lower limbs to treat superficial and deep microcirculatory disturbances.

The salts according to the invention can be applied topically to treat Raynaud's disease, scleroderma, acrocyanosis and other forms of atherosclerosis of the limbs (heavy legs, intermittent claudication, etc.). In diseases of this type the products act by increasing the capillary blood flow in the tissues by acting on the myocytes in the capillary arterioles and prearterioles.

The products also have cosmetic applications in conditions where the superficial microcirculation is impaired by atherosclerosis due to aging and in the treatment of cellulitis.

The new salts according to the invention produce better results than the basic alkaloids (i.e. the pharmacologically active, naturally occurring or synthetic alkaloid, or alkaloid derivative used to form the salts) under these conditions because they are better distributed in the surface tissue and remain present at the site of action for longer periods of time.

DETAILED DESCRIPTION

The examples given below serve to illustrate the invention without in any way limiting its scope.

EXAMPLE I

Preparation of ethyl apovincaminate dipalmitoyl glycerylphosphatidate 3.50 g ethyl apovincaminate base are dissolved in 15 ml methylene chloride with stirring and 6.48 g dipalmitoyl glyceryl phosphatidic acid added at ambient temperature.

When the reagents have dissolved completely, the solution in methylene chloride is evaporated to dryness under vacuum at a temperature not exceeding 40° C. until the solvent has been completely eliminated. The residue is dispersed in n-hexane at 5° C. and filtered. This yields 9.95 g of a white solid with the following characteristics:

m.p. 50° C. ca
$[\alpha]_D = +50.13°(c=0.5$ in $CHCl_3)$
$31_{P-NMR}$ 2.65 ppm

EXAMPLE II

Preparation of the salt of ethyl apovincaminate with hydrogenated soya phosphatidic acid 3.50 g ethyl apovincaminate base are dissolved in 15 ml methylene chloride with stirring and 7 g hydrogenated soya phosphatidic acid (natural ratio of fatty acids) with a mean molecular weight determined by acid-base titration of 698 are added. When the reagents have dissolved completely, the solution in methylene chloride is evaporated to dryness under vacuum at a temperature not exceeding 40° C. until the solvent has been completely eliminated. The residue is dispersed in n-hexane at 5° C. and filtered. This yields 10.5 g of a white solid with the following characteristics:

m.p. 52.8° C.
$[\alpha]_D = 27.8°(Conc = 1\%$ $CHCl_3).$
$31_{P-NMR}$ 2.65, 4.06 ppm

EXAMPLE III

Preparation of the salt of nicergoline with hydrogenated soya phosphatidic acid 4.84 g ethyl apovincaminate base are dissolved in 50 ml methylene chloride with stirring and 7 g hydrogenated soya phosphatidic acid (natural ratio of fatty acids) with a mean molecular weight determined by acid-base titration of 698 are added. When the reagents have dissolved completely, the solution in methylene chloride is evaporated to dryness under vacuum at a temperature not exceeding 40° C. until the solvent has been completely eliminated. The residue is dispersed in n-hexane at 5° C. and filtered.

This yields 11.7 g of a white solid with the following characteristics:

m.p. 150°–190° C. (dec.)
$[\alpha]_D = +12.16°(c=0.5$ in $CHCl_3)$

EXAMPLE IV

Preparation of the salt of vincamine with hydrogenated soya phosphatidic acid 3.54 g vincamine base are dissolved in 15 ml methylene chloride with stirring and 7 g hydrogenated soya phosphatidic acid (natural ratio of fatty acids) with a mean molecular weight determined by acid-base titration of 698 are added. When the reagents have dissolved completely, the solution in methylene chloride is evaporated to dryness under vacuum at temperature not exceeding 40° C. until the solvent has been completely eliminated. The residue is dispersed in n-hexane at 5° C. and filtered. This yields 10.5 g of a white solid with the following characteristics:

$[\alpha]_D = -4.9°(c=0.5$ in $CHCl_3)$
$31_{P-NMR}$ 2.56, 4.21 ppm

EXAMPLE V

Preparation of nicergoline dipalmitoyl-glyceryl phosphatidate 4.84 g of nicergoline base are dissolved in 50 ml methylene chloride with stirring and 6.48 g dipalmitoyl glyceryl phosphatidic acid are added at ambient temperature. When the reagents have dissolved completely, the solution in methylene chloride is evaporated to dryness under vacuum at a temperature not exceeding 40° C. until the solvent has been completely eliminated. The residue is dispersed in n-hexane at 5° C. and filtered. This yields 11.1 g of a white solid with the following characteristics:

$[\alpha]_D = +10.14°(c=0.5$ in $CHCl_3)$

EXAMPLE VI

Preparation of the salt of raubasine with hydrogenated soya phosphatidic acid 3.52 g raubasine base are suspended in 100 ml methylene chloride with stirring and 7 g hydrogenated soya phosphatidic acid (natural ratio of fatty acids) with a mean molecular weight determined by acid-base titration of 698 are added. When the reagents have dissolved completely, the solution in methylene chloride is evaporated to dryness under vacuum at a temperature not exceeding 40° C. until the solvent has been completely eliminated. The residue is dispersed in n-hexane at 5° C. and filtered. This yields 10.3 g of a white solid with the following characteristics:

$[\alpha]_D = 26.5°(c=0.5$ in $CHCl_3)$
$31_{P-NMR}$ 1.22, 2.38 ppm

EXAMPLE VII

Preparation of plasters for transdermal absorption containing the nicergoline salt of hydrogenated soya phosphatidic acid The nicergoline salt of hydrogenated soya phosphatidic acid is incorporated in an adhesive mass that controls the release of the drug and has the following composition:

| nicergoline salt of phosphatidic acid | 50 mg |
|---|---|
| lactose | 398 mg |
| saturated triglycerides | 22 mg |
| polyisobutene | 220 mg |
| hydrogenated colophony | 195 mg |
| polyalkadiene | 195 mg |

The transdermal plaster is made up of three layers, namely a backing sheet, an adhesive film containing the active principle built up by forming several coatings, and a cover sheet. The drug is released over a period of 24 h to ensure continuous administration.

EXAMPLE VII

Preparation of a lipogel containing the salt of ethyl apovincaminate with hydrogenated soya phosphatidic acid The formulation used to prepare 100 kg lipogel comprises the following reagents:

| ethyl apovincaminate salt of phosphatidic acid | 1 kg |
|---|---|
| cholesterol | 0.5 kg |
| alcohol | 8 kg |
| butyl hydroxytoluene | 0.01 kg |
| imidazozolynidylurea | 0.30 kg |
| dehydroacetic acid and salts (Prevan) | 0.20 kg |
| sodium edetate | 0.15 kg |
| hydroxypropylmethyl cellulose | 2.00 kg |
| water | 87.84 kg |

We claim:

1. A salt having the formula $$[Alk]_x[PA]_y$$

wherein

Alk is a cation derived from an alkaloid selected from the group consisting of vincamine, apovincamine, raubasine, apocuanzine, nicergoline and salts and esters thereof, PA represents a phosphatidic acid or a mixture of phosphatidic acids represented by the formula

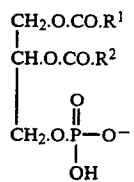

wherein $R^1$ and $R^2$ which may be the same or different represent a $C_{10-24}$ alkyl group, a $C_{10-24}$ alkenyl group or a $C_{10-24}$ alkadienyl group, and x:y is a substantially equimolar ratio in the range 1.1:1 to 1:1.1.

2. A salt according to claim 1 wherein Alk is a cation derived from an alkaloid selected from the group consisting of vincamine, ethyl apovincaminate, raubasine, apocuanzine and nicergoline.

3. A salt having the formula $$[Alk]_x[PA]_y$$

wherein

Alk is a cation derived from an alkaloid selected from the group consisting of vincamine, ethyl apovincamine, raubasine, apocuanzine and nicergoline, PA represents a phosphatidic acid or a mixture of phosphatidic acids represented by the formula

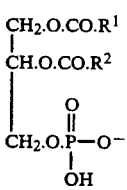

wherein $R^1$ and $R^2$ which may be the same or different represent a $C_{10-24}$ alkyl group, a $C_{10-24}$ alkenyl group or a $C_{10-24}$ alkadienyl group, and x:y is a substantially equimolar ratio in the range 1.1:1 to 1:1.1.

4. A salt according to claim 3 wherein $R^1$ and $R^2$ represent a $C_{15-24}$ alkyl group, a $C_{15-24}$ alkenyl group or a $C_{15-24}$ alkadienyl group.

5. A salt according to claim 4 wherein $R^1$ and $R^2$ represent a $C_{15-24}$ alkyl group, a $C_{15-17}$ alkenyl group or a $C_{15-17}$ alkadienyl group.

6. A salt according to claim 1, wherein $R^1$ and $R^2$ represent a $C_{15-24}$ alkyl group, a $C_{15-24}$ alkenyl group or a $C_{15-24}$ alkadienyl group.

7. A salt according to claim 6, wherein $R^1$ and $R^2$ represent a $C_{15-17}$ alkyl group, a $C_{15-17}$ alkenyl group or a $C_{15-17}$ alkadienyl group.

8. A method of producing a salt as claimed in claim 1 which comprises reacting an alkaloid with a phosphatidic acid, said reaction being carried out in a solvent for said alkaloid and phosphatidic acid.

9. A salt according to claim 8 wherein the alkaloid is nicergoline.

10. A salt according to claim 1 wherein the alkaloid is ethyl apovincaminate.

11. A method according to claim 8 wherein the solvent is selected from the group consisting of halogenated hydrocarbons, ketones, ethers and mixtures thereof.

* * * * *